United States Patent
Gruber et al.

(10) Patent No.: US 6,463,615 B1
(45) Date of Patent: Oct. 15, 2002

(54) TOOTHBRUSH HAVING MAIN BRISTLES AND HAVING TRANSVERSELY AND LONGITUDINALLY ADJUSTABLE INTERDENTAL BRISTLES

(75) Inventors: Paul Gruber, Klagenfurt; Christian Mikula, Wernberg; Gerald Kauer, Ferlach, all of (AT); Jan Peter Elkhuizen, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 2 days.

(21) Appl. No.: 09/694,169

(22) Filed: Oct. 23, 2000

(30) Foreign Application Priority Data

Oct. 29, 1999 (EP) ............................................. 99890349

(51) Int. Cl.⁷ ............................................. A46B 13/02
(52) U.S. Cl. ............................................. 15/22.1; 15/28
(58) Field of Search ..................................... 15/22.1, 28

(56) References Cited

U.S. PATENT DOCUMENTS

| 5,836,030 A | 11/1998 | Hazeu et al. |
| 6,237,178 B1 * | 5/2001 | Krammer et al. |
| 6,308,358 B2 * | 10/2001 | Gruber et al. |

FOREIGN PATENT DOCUMENTS

WO     97/07707     3/1997

* cited by examiner

Primary Examiner—Randall E. Chin
(74) Attorney, Agent, or Firm—Ernestine C. Bartlett

(57) ABSTRACT

A toothbrush (1) has a cleaning member (3) equipped with a drivable bristle holder (20) for holding main bristles (21) and with a drivable interdental bristle holder (26) for holding interdental bristles (27), the interdental bristle holder (26) being coupled to a drive element (29) with the aid of a coupling element (39) and, of the coupling element (39) and the drive element (29) at the coupling element (39) is at least partly elastically deformable parallel to the longitudinal bristle direction (28) of the interdental bristles (27) held by the interdental bristle holder (26).

12 Claims, 3 Drawing Sheets

TOOTHBRUSH HAVING MAIN BRISTLES AND HAVING TRANSVERSELY AND LONGITUDINALLY ADJUSTABLE INTERDENTAL BRISTLES

BACKGROUND OF THE INVENTION

Toothbrush having main bristles and having transversely and longitudinally adjustable interdental bristles The invention relates to a toothbrush having a grip member and having a cleaning member, which is connected to the grip member and which extends substantially parallel to a cleaning-member longitudinal direction, and having drive means, which are partly accommodated in the grip member and partly in the cleaning member and which include a drivable first drive element and a drivable second drive element in the cleaning member in the area of that end of the cleaning member which is remote from the grip member, and having a drivable bristle holder which holds a plurality of main bristles and which is coupled to the first drive element with the aid of a first coupling element, and having a drivable interdental bristle holder, which holds a plurality of interdental bristles which extend substantially parallel to a longitudinal bristle direction, which is oriented transversely to the cleaning-member longitudinal direction, and which is coupled to the second drive element with the aid of a second coupling element.

The invention further relates to a cleaning member which extends substantially parallel to a cleaning-member longitudinal direction, and which has drive means, which include a drivable first drive element and a drivable second drive element in the area of one. end of the cleaning member, and which has a drivable bristle holder, which holds a plurality of main bristles and which is coupled to the first drive element with the aid of a first coupling element, and which has a drivable interdental bristle holder, which holds a plurality of interdental bristles which extend substantially parallel to a longitudinal bristle direction, which is oriented transversely to the cleaning-member longitudinal direction, and which is coupled to the second drive element with the aid of a second coupling element.

A toothbrush and a cleaning member as defined above are known from the patent document U.S. Pat. No. 5,836,030 A. Such a toothbrush has been put on the market by the Applicant and has proved to be comparatively successful. In order to obtain a satisfactory overall cleaning result with such a toothbrush, as well as with any other toothbrush, it is very important to achieve a good cleaning action in the interdental areas. In this respect it has proved to be disadvantageous with the known toothbrush and with the known cleaning member that the second coupling element and the second drive element are of a stiff construction and consequently form a more or less rigid unit.

SUMMARY OF THE INVENTION

It is an object of the invention to provide an improved cleaning action in a simple manner and by simple means both at the main dental areas and in the interdental areas and thus achieve an improved overall cleaning result with a toothbrush and with a cleaning member as defined above.

According to the invention, in order to achieve the aforementioned object, t a toothbrush of the type defined above is provided in which of the second coupling element and the second drive element, at least the second coupling element is at least partly elastically deformable substantially parallel to the longitudinal bristle direction of the interdental bristles.

According to the invention, in order to achieve the aforementioned object, a cleaning member is provided in a toothbrush of the type defined above in which of the second coupling element and the second drive element, at least the second coupling element is at least partly elastically deformable substantially parallel to the longitudinal bristle direction of the interdental bristles.

By providing the characteristic feature in accordance with the invention an improved cleaning action is achieved at the main tooth areas with a toothbrush in accordance with the invention and with a cleaning member in accordance with the invention, because at these areas the mostly longer interdental bristles recede and, as a result of this, both the interdental bristles and the main bristles, which are disposed directly adjacent the interdental bristles, are capable of providing an intensive cleaning contribution. In addition, an improved cleaning action in the interdental areas is achieved because the interdental bristles perform not only a movement substantially parallel to the interdental areas but, in addition, can also perform a movement perpendicularly to the interdental areas and perpendicularly to the main tooth areas. In this respect it is very essential that the aforementioned additional movement of the interdental bristles is independent of the relative position of the interdental bristle holder with respect to the bristle holder, as a result of which the interdental bristle holder and, consequently, the interdental bristles can perform a movement which is oriented substantially parallel to the longitudinal bristle-direction of the interdental bristles. This is true also in the case when the interdental bristle holder is pivotable owing to the elastic deformability of at least the second coupling element and, when applicable, also of the second drive element, because in this case a comparatively large pivoting radius, i.e. a comparatively long lever arm, which is independent of the relative position with respect to the bristle holder, can be obtained for the interdental bristle holder.

It is to be noted that from the patent document WO 97/07707 A1 a toothbrush is known in which a bristle holder and an interdental bristle holder have been provided but in which neither the bristle holder nor the interdental bristle holder is drivable with the aid of drive elements of drive means and in which the interdental bristle holder is connected directly to the bristle holder. Although in this case the connection between the bristle holder and the interdental bristle holder is elastically deformable, the interdental bristle holder can perform only a pivotal movement defined by the elastically deformable connection between the bristle holder and the interdental bristle holder, i.e. a pivotal movement which is dependent on the relative position of the interdental bristle holder with respect to the bristle holder, in other words a pivotal movement having only a comparatively small pivoting radius, i.e. a comparatively short lever arm, which is less favorable for the cleaning of the interdental areas because the interdental bristles perform not only a movement substantially parallel to the longitudinal brush-direction of the interdental bristles but, with their free ends, also a movement oriented transversely to the longitudinal brush-direction of the interdental bristles and transversely to the interdental areas, which is less favorable for a deep cleaning of the interdental areas.

Both the second coupling element and the second drive element of a toothbrush and a cleaning member in accordance with the invention can be of an elastically deformable construction, which is particularly favorable in order to obtain a lever arm of maximal length. However, it has proved to be very advantageous when, in addition, a toothbrush and a cleaning member are provided in accordance with the invention wherein the second coupling element is formed by a metal blade spring configuration having a first end portion, an intermediate portion and a second end portion, the interdental bristle holder is connected to the first end portion, and the second drive element is connected to the second end portion. This has proved to be particularly advantageous in view of a construction which is as simple and reliable as possible.

Moreover, it has proved to be very advantageous when, in addition, the characteristic features are provided in a toothbrush wherein the second drive element consists of a plastic, and the connection between the second end portion and the second drive element is formed by an injection-molded connection and/or wherein the interdental bristle holder consists of a plastic, and the connection between the first end portion and the interdental bristle holder is formed by an injection-molded connection. This has proved to be very favorable in view of a construction which is as simple and reliable as possible.

However, it has also proved to be very advantageous when, in addition, the characteristic features are provided in a toothbrush wherein the second drive element and the second coupling element as well as the interdental bristle holder consist of an integral part made of a comparatively hard plastic, and the second coupling element is constructed as a bending element, and at least the second coupling element is embedded in a cover which consists of a comparatively soft plastic. In especially preferred embodiments, the comparatively hard plastic is polyoxymethylene, and the comparatively soft plastic is a thermoplastic elastomer. This enables a solution that is particularly favorable with regard to the pivotal movement of the interdental bristle holder to be realized because the flexural element guarantees stability and the soft component surrounding the flexural element damps the deflection movements in an advantageous manner.

The above-mentioned as well as further aspects of the invention will become apparent from the two embodiments described hereinafter by way of example and will be elucidated with reference to these two examples.

BRIEF DESCRIPTION OF THE DRAWINGS

The invention will now be described in more detail with reference to the drawings, which show two embodiments given by way of example but to which the invention is not limited.

DESCRIPTION OF THE PREFERRED EMBODIMENTS

Figure 1:
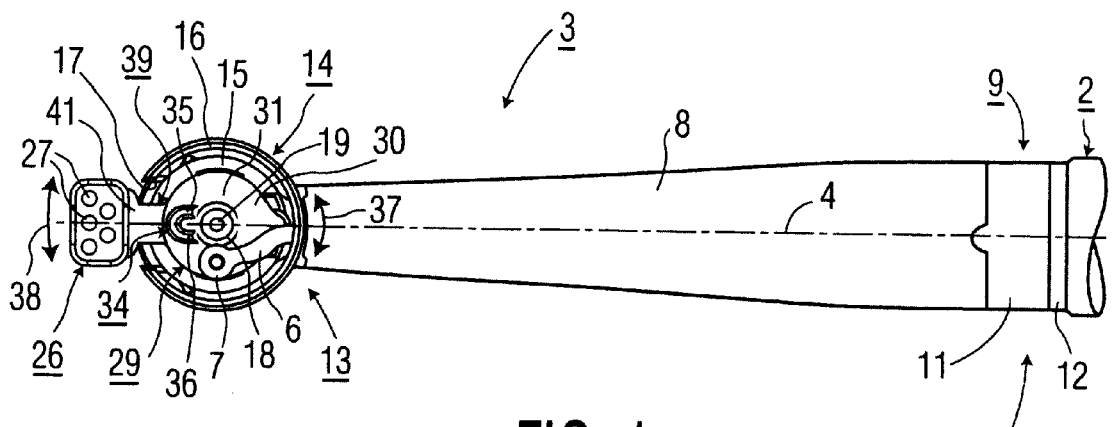
FIG. 1 is a plan view which shows the relevant part of a toothbrush in accordance with a first embodiment of the invention, which toothbrush has a cleaning member in accordance with a first embodiment of the invention.
Figure 2:
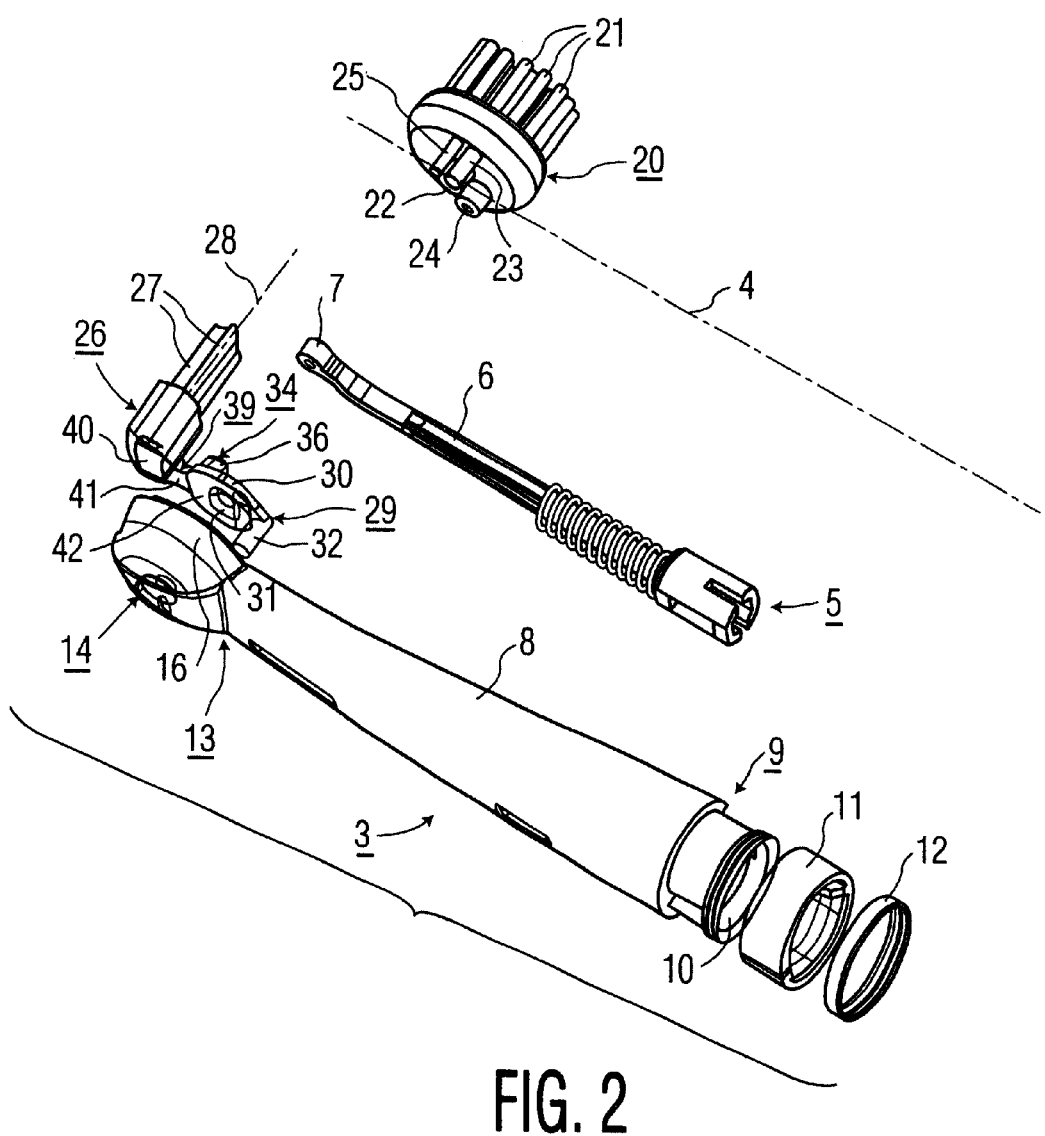
FIG. 2 is an exploded view which shows the cleaning member of the toothbrush shown in FIG. 1.

FIG. 1 shows a part of a toothbrush 1. The toothbrush 1 comprises a grip member 2, which is shown in FIG. 1 only, and a cleaning member 3 connected to the grip member 3. The cleaning member 3 extends parallel to a longitudinal direction 4 of the cleaning member, which direction is shown as the longitudinal axis 4 of the cleaning member 3 in FIGS. 1 and 2.

The toothbrush 1 has drive means 5, which are accommodated partly in the grip member 2 and partly in the cleaning member 3. For the construction of the drive means 5 reference is made to the patent document U.S. Pat. No. 5,836,030 A. The subject matter disclosed in said patent document is incorporated herein by the reference to said document. The part of the drive means 5 of the toothbrush 1 shown partly in FIG. 1, which is accommodated in the cleaning member 2, is wholly identical to the drive means described in the patent document U.S. Pat. No. 5,836,030 A.

The part of the drive means 5 accommodated in the cleaning member 3 comprises a connecting rod 6 which is reciprocatingly drivable parallel to the longitudinal direction 4 of the cleaning member. The connecting rod 6 is equipped with a first drive element 7 in the area of its free end. In the present case the first drive element 7 consists of a drive socket.

The cleaning member 3 is made of a plastic and is essentially tubular. The cleaning member 3 has a tubular portion 8. In the area of the end 9 of the cleaning member 3, which end faces the grip member 2, the cleaning member 3 has a coupling portion 10 which is integral with the tubular portion 8 provided and adapted to couple the cleaning member 3 to the grip member 2. The coupling portion 10 carries an indicator ring 11 which is locked by means of a retaining ring 11. At the end 13 of the cleaning member 3, which end is remote from the grip member 2, the cleaning member 3 has a head portion 14 which is essentially pot-shaped. As is apparent from FIG. 1—in which a bristle holder 30 including main bristles 21 is not shown—the head portion 14 has a pot bottom wall 15 and a circumferential pot wall 16. In the area of the end which is remote from the tubular portion 8 the circumferential pot wall 16 has an aperture 17, the purpose of which will be described hereinafter.

Figures 3, 6:
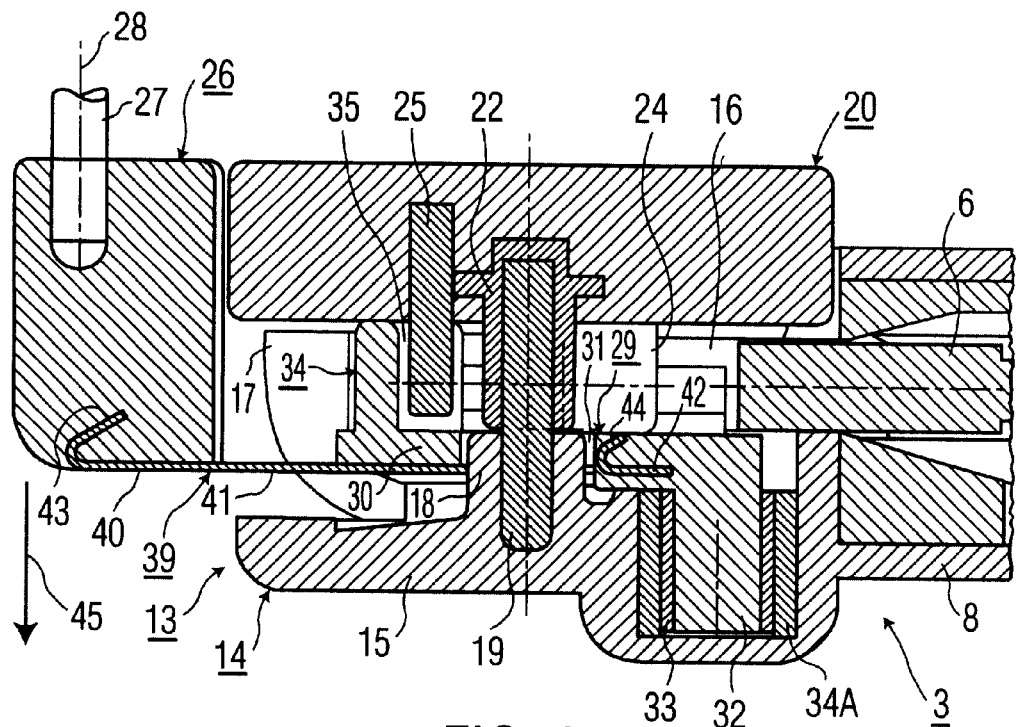
FIG. 3 is a sectional view taken at the location of the free end of the cleaning member shown in FIG. 2.
FIG. 6 shows, in the same way as FIG. 3, the area of the free end of the cleaning member shown in FIG. 5.

As is apparent from FIG. 3, a bearing sleeve 18 projects from the pot bottom wall 15 of the head portion 14 and is-integral with the head portion 14. A metal bearing spindle 19 is a press-fit in the bearing sleeve 18.

The cleaning member 3 is equipped with a drivable bristle holder 20, which carries a plurality of main bristles 21, which for the sake of simplicity are not shown in FIG. 3. The bristle holder 20 consists of a plastic. A bearing sleeve 22 is connected to the bristle holder 20, the connection between the bearing sleeve 22 and the bristle holder 20 being formed by molding around the bearing sleeve 22. The bearing sleeve 22 projects from the bristle holder 20 towards the head portion 14 and is mounted on the bearing spindle 19, a reciprocating movement in tangential directions being possible between the bearing spindle 19 and the bearing sleeve 22. Locking hooks, not shown, project from the bristle holder 20 in radial directions and engage a circumferential groove, not shown either, in the circumferential pot wall 16, thereby locking the bristle holder 20 in axial directions.

Further, a coupling pin, which extends parallel to the bearing sleeve 22, projects from the bristle holder 20 towards the head portion 14 and forms a first coupling element 23 of the cleaning member 3. The coupling pin forming the first coupling element 23 projects into the drive socket which forms the first drive element 7 of the cleaning member 3.

Thus, the bristle holder 20 is coupled to the first drive element 7 and, consequently, to the drive means 5 with the aid of the first coupling element 23.

Further, a hold-down ring 24, which extends parallel to the bearing sleeve 22 and to the coupling pin forming the first coupling element 23, projects from the bristle holder 20 towards the head portion 14 and serves to hold down a second drive element for driving an interdental bristle holder, as will be described in more detail hereinafter.

Further, a drive pin 25 projects from the bristle holder 20 towards the head portion 14, which drive pin is connected to the bristle holder 20 by molding and forms part of the drive means 5, its purpose being described hereinafter.

The cleaning member 3 is further equipped with a drivable interdental bristle holder 26, which carries a plurality-of interdental bristles 27, which extend parallel to a longitudinal bristle-direction 28, which is oriented transversely to the longitudinal direction 4 of the cleaning member. For the sake of simplicity the interdental bristles 27 are merely indicated in FIG. 3. In order to drive the interdental bristle holder 26 the cleaning member 3 has a second drive element 29. The second drive element 29 has a drive disc 30 having a central slot 31 which is engaged the bearing sleeve 18, which projects from the head portion 14, without the actuating movement of the drive disc 30 and, consequently, of the second drive element 29 being impaired. A bearing pin 32 projects from the drive disc 30 in a direction towards the pot bottom wall 15 of the head portion 14 in the disc area which faces the tubular portion 8. A first bearing sleeve 33 is a press-fit on the bearing pin 32. The first bearing sleeve 33 cooperates with a stationary second bearing sleeve 34A, which second bearing sleeve 34A is locked in rotation to the head portion 14 of the cleaning member 3 by molding. A relative movement in tangential directions is possible between the bearing sleeve 33 and the second bearing sleeve 34A, thus enabling a reciprocatory pivotal movement to be performed by the second drive element 29. The second drive element 29 is axially positioned with the aid of the head portion 14 and with the aid of the hold-down ring 24.

A coupling member 34, which is U-shaped in plan view, projects from the drive disc 30 in its area which is remote from the tubular portion 8, which coupling member is integral with the drive disc 30 and has two limb walls 35 and 36. The drive pin 25, which projects from the bristle holder 20, engages between the two limb walls 35 and 36.

When the drive means 5 are driven during operation of the toothbrush 1 this causes the connecting rod 6 to be reciprocated parallel to the longitudinal direction 4 of cleaning member. As a result of this, the first coupling element 23, i.e. the coupling pin, is reciprocated via the first drive element 7, i.e. via the drive socket, as a result of which the bristle holder 20 and, consequently, the main bristles carried by this holder perform a reciprocatory movement as indicated by the double arrow 37 (see FIG. 1). The pivotal movement of the bristle holder 20 causes the drive pin 25 to also perform a corresponding pivotal movement, which the drive pin 25 imparts to the drive disc 30, and hence to the second drive element 29, via the coupling member 34, i.e. via the two limb walls 35 and 36 of the coupling member 34. As a result of this, the second drive element 29 performs a reciprocatory pivotal movement as indicated by the double arrow 38 (see FIG. 1) about the second bearing sleeve 34, which in its turn causes the interdental bristle holder 28 to also perform a reciprocatory pivotal movement as indicated by the double arrow 38, because the interdental bristle holder 26 is coupled to the second drive element 29 with the aid of a second coupling element 39, which extends through the aperture 17 in the circumferential pot wall 16.

In the case of the toothbrush 1 shown in FIG. 1 and the cleaning member 3 of this toothbrush 1 the construction in the area of the bristle holder 20 and in the area of the interdental bristle holder 26 is such that both the second coupling element 39 and the second drive element 29 are partly elastically deformable substantially parallel to the longitudinal bristle direction 28 of the interdental bristles 27. In the present case the second coupling element 39 is formed by a metal blade spring configuration. The blade spring configuration provided as the second coupling element 39 has a first end portion 40, an intermediate portion 41, and a second end portion 42. The interdental bristle holder 26 is fixedly connected to the first end portion 40. The second drive element 29, i.e. the drive disc 30 of the second drive element 29, is fixedly connected to the second end portion 42. The connection between the first end portion 40 and the interdental bristle holder 26, which consists of a plastic, is formed by an injection-molded connection. In order to improve the reliability of the injection-molded connection between the interdental bristle holder 26 and the first end portion 40 the blade spring configuration has a first bent portion 43 in the area of the first end portion 40. The connection between the second end portion 42 of the blade spring configuration forming the second coupling element 39 and the second drive element 29 is likewise formed by an injection-molded connection. In order to improve the reliability of the injection-molded connection formed by molding around the second end portion 42 the blade spring configuration has a second bent portion 44 in the area of the second end portion 42.

In the construction shown in FIG. 3 the second drive element is very stable and rigid in the area of the connection between the bearing pin 32 and the drive disc 30, and the second drive element 29 is elastically deformable parallel to the longitudinal bristle direction 28 in the area in which the slot 31 is situated, as a result of which the drive disc 30 can deflect in the direction indicated by an arrow 45 in its area where it carries the coupling member 34, in which case the drive disc 30 is deformed elastically. Furthermore, the blade spring configuration forming the second coupling element 39 can readily deform elastically, particularly in its central portion 41, as a result of which a suitable deflection in the direction indicated by the arrow 45 is achieved in this area. This deflection is limited in that the central portion 41 abuts against the pot bottom wall 15 of the head portion 14.

As a result of the afore-mentioned elastic deformability of the second drive element 29 and of the blade spring configuration forming the second coupling element 39 in portions of these two elements 29 and 39, it is achieved that the interdental bristle holder 26 and, consequently, the interdental bristles 27 carried by this holder are movable in the direction indicated by the arrow 45 and the interdental bristles 27 can thus perform movement substantially parallel to its longitudinal bristle direction 28, which movement is essentially a pivotal movement performed with a comparatively large lever arm. Such a pivotal movement capability of the interdental bristles 27 has proved to be very advantageous in view of a proper cleaning action both in the area of the lateral main tooth surfaces and in the area of the interdental spaces between these lateral main tooth surfaces.

Figure 4:
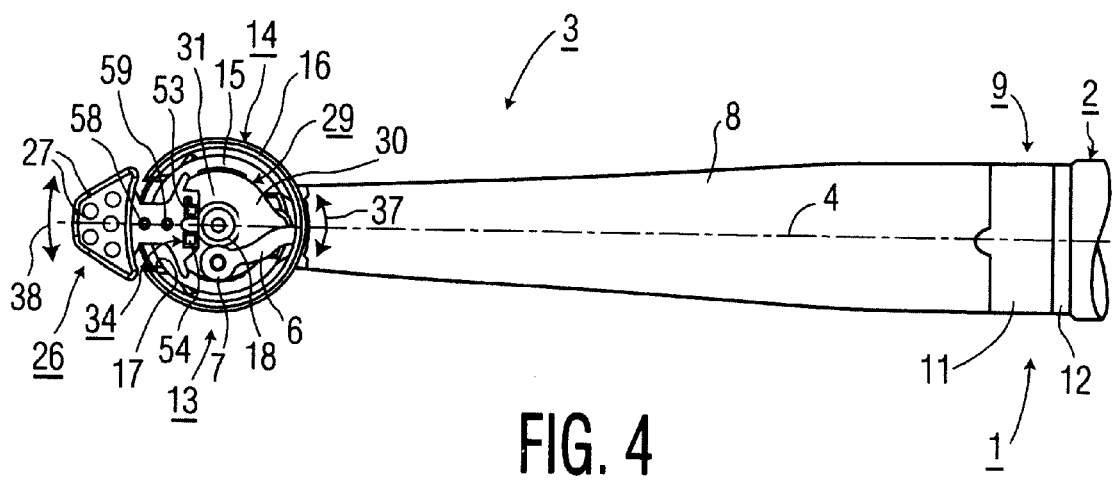
FIG. 4 shows, in the same way as FIG. 1, a toothbrush in accordance with a second embodiment of the invention, which toothbrush has a cleaning member in accordance with a second embodiment of the invention.

FIG. 4 shows, in the same way as FIG. 1, a part of a toothbrush 1. The toothbrush 1 shown in FIG. 4 is of the same construction as the toothbrush 1 in FIG. 1 as regards the grip member 2 and as regards the tubular portion 8 and the coupling portion 10 of the cleaning member 3.

As is apparent from FIG. 6, the construction of the mounting arrangement of the bristle holder 20 and the mounting arrangement of the second drive element 29 in the toothbrush 1 as shown in FIG. 4 are different from those in the toothbrush as shown in FIG. 1.

In the present case, the bristle holder 20 has a sleeve-shaped projection 49 and a bore 50 which traverses the bristle holder 20 and the projection 49 and which is stepped in the area of its end which faces the main bristles 21. A bearing sleeve 51 engages in the bore 50 and is curved at its end which faces the head portion 14. A metal bearing pin 52 extends through the bearing sleeve 51 and is secured in the head portion 14 by a press-fit. A tangential reciprocatory movement is possible between the bearing pin 52 and the bearing sleeve 51.

In the same way as in the case of the cleaning member 3 shown in FIG. 3, the second drive element 29 has a drive disc 30. The drive disc 30 also has a bearing pin 32 which is integral with it. The bearing pin 32 is reciprocatingly movable in tangential directions with respect to a bearing sleeve 34A. The bearing sleeve 34A is immobilized in the head portion 14 by molding.

The second drive element 29 also has a coupling member 34, which in the present case is formed by two projections 53 and 54 which extend from the drive disc 30 towards the bristle holder 20. The drive pin 25 engages between the two projections 53 and 54.

Figure 5:
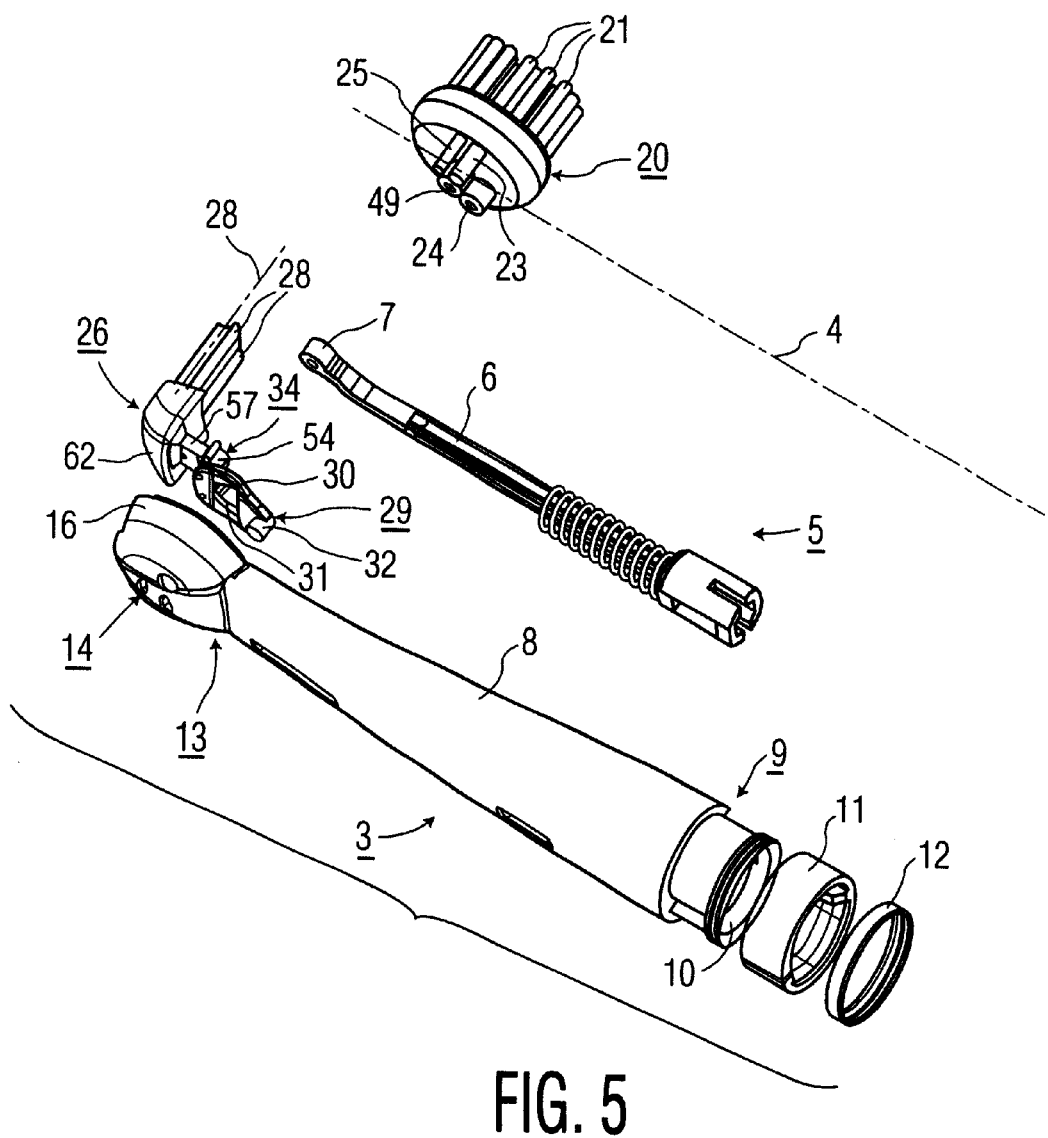
FIG. 5 shows, in the same way as FIG. 2, the cleaning member of the toothbrush shown in FIG. 4.

In the embodiment shown in FIGS. 4, 5 and 6 the second drive element 29, the second coupling element 39 and the interdental bristle holder 26 form an integral part made of a comparatively hard plastic. The second coupling element 39 takes the form of a bending element. The bending element forming the second coupling element 39 has a first end 55 and a second end 56. In the area of the first end 55 the bending element is integral with the interdental bristle holder 26. In the area of the second end 56 the bending element is fixedly connected to the two projections 53 and 54 of the coupling member 34, so that in this way the bending element forming the second coupling member 39 is fixedly connected to the drive disc 30, and consequently to the second drive element 29, via the projections 53 and 54.

The bending element forming the second coupling element 39 is embedded in a cover of a comparatively soft plastic. For securely connecting the cover 57 to the second coupling element 39 a total of three projections 58, 59 and 60 project from the second coupling element 39 and are substantially cylindrical. Thus, an interlocking connection to the cover 57 is realized by means of the three projections 58, 59 and 60. The third projection 60 at the same time constitutes a limiting stop, which cooperates with a stop surface 61 on the head portion 14 and thus limits a movement of the interdental bristle holder 26 in the direction indicated by the arrow 45. In the present case the cover 57 in addition has a cap-shaped extension 62, which covers a part of the interdental bristle holder 26 and which has a bent portion 64 in the area of its free end 63. The bent portion 64 also forms an interlocking connection, so that altogether the cover 57 is retained properly and reliably.

It is to be noted that the comparatively hard plastic of which the second drive element 29, the second coupling element 39 and the interdental bristle holder 26 are made is polyoxymethylene. The comparatively soft plastic of which the cover 57 is made is a thermoplastic elastomer.

In the embodiment of the toothbrush 1 shown in FIG. 4 and of the cleaning member 3 shown in FIGS. 5 and 6 the movement of the interdental bristle holder 26 in the direction indicated by the arrow 45 is achieved by virtue of the partly elastic deformability of two parts, namely the elastic deformability of the second coupling element 39 formed by the bending element and also the elastic deformability of the drive disc 30, namely in the area where the two projections 53 and 54 are connected to the drive disc 30. In this embodiment this also results in a comparatively long lever arm for the movement of the interdental bristle holder 26 in the direction indicated by the arrow 45.

What is claimed is:

1. A toothbrush having a grip member and
having a cleaning member, which is connected to the grip member and which extends substantially parallel to a cleaning-member longitudinal direction, and
having drive means, which are partly accommodated in the grip member and partly in the cleaning member and which include a drivable first drive element and a drivable second drive element in the cleaning member in the area of that end of the cleaning member which is remote from the grip member, and
having a drivable bristle holder, which holds a plurality of main bristles and which is coupled to the first drive element, with the aid of a first coupling element, and having a drivable interdental bristle holder, which holds a plurality of interdental bristles which extend substantially parallel to a longitudinal bristle direction, which is oriented transversely to the cleaning-member longitudinal direction, and which is coupled to the second drive element with the aid of a second coupling element, wherein,
of the second coupling element and the second drive element, at least the second coupling element is at least partly elastically deformable substantially parallel to the longitudinal bristle direction of the interdental bristles.

2. A toothbrush as claimed in claim 1, wherein
the second coupling element is formed by a metal blade spring configuration having a first end portion, an intermediate portion and a second end portion, and
the interdental bristle holder is connected to the first end portion, and
the second drive element is connected to the second end portion.

3. A toothbrush as claimed in claim 2, wherein
the second drive element consists of a plastic, and
the connection between the second end portion and the second drive element is formed by an injection-molded connection.

4. A toothbrush as claimed in claim 2, wherein
the interdental bristle holder consists of a plastic, and
the connection between the first end portion and the interdental bristle holder is formed by an injection-molded connection.

5. A toothbrush as claimed in claim 1, wherein
the second drive element and the second coupling element as well as the interdental bristle holder consist of an integral part made of a comparatively hard plastic, and
the second coupling element is constructed as a bending element, and
at least the second coupling element is embedded in a cover which consists of a comparatively soft plastic.

6. A toothbrush as claimed in claim 5,
the comparatively hard plastic is polyoxymethylene, and
the comparatively soft plastic is a thermoplastic elastomer.

7. A cleaning member for a toothbrush, which cleaning member extends substantially parallel to a cleaning-member longitudinal direction, and which has drive means, which include a drivable first drive element and a drivable second drive element in the area of one end of the cleaning member, and which has a drivable bristle holder, which holds a plurality of main bristles and which is coupled to the first drive element with the aid of a first coupling element, and which has a drivable interdental bristle holder, which holds a plurality of interdental bristles which extend substantially parallel to a longitudinal bristle direction, which is oriented transversely to the cleaning-member longitudinal direction, and which is coupled to the second drive element with the aid of a second coupling element, wherein, of the second coupling element and the second drive element, at least the second coupling element is at least partly elastically deformable substantially parallel to the longitudinal bristle direction of the interdental bristles.

8. A cleaning member as claimed in claim 7, wherein the second coupling element is formed by a metal blade spring configuration having a first end portion, an intermediate portion and a second end portion, and the interdental bristle holder is connected to the first end portion, and the second drive element is connected to the second end portion.

9. A cleaning member as claimed in claim 8, wherein the second drive element consists of a plastic, and the connection between the second end portion and the second drive element is formed by an injection-molded connection.

10. A cleaning member as claimed in claim 8, wherein the interdental bristle holder consists of a plastic, and the connection between the first end portion and the interdental bristle holder is formed by an injection-molded connection.

11. A cleaning member as claimed in claim 7, wherein the second drive element and the second coupling element as well as the interdental bristle holder consist of an integral part made of a comparatively hard plastic, and the second coupling element is constructed as a bending element, and at least the second coupling element is embedded in a cover which consists of a comparatively soft plastic.

12. A cleaning member as claimed in claim 11, wherein the comparatively hard plastic is polyoxymethylene, and the comparatively soft plastic is a thermoplastic elastomer.

* * * * *